United States Patent [19]

Panalletta

[11] Patent Number: 5,121,751

[45] Date of Patent: Jun. 16, 1992

[54] INSTRUMENT FOR TISSUE SAMPLING

[75] Inventor: Joseph V. Panalletta, Guntersville, Ala.

[73] Assignees: Ryder International Corporation, Arab, Ala. ; a part interest; Meadox Medicals, Inc., Oakland, N.J. ; a part interest

[21] Appl. No.: 495,427

[22] Filed: Mar. 16, 1990

[51] Int. Cl.⁵ .............................................. A61B 10/00
[52] U.S. Cl. ................................................... 128/754
[58] Field of Search ......................... 128/749, 753–755; 606/167, 170

[56] References Cited

U.S. PATENT DOCUMENTS

| | | |
|---|---|---|
| 1,867,624 | 7/1932 | Hoffman . |
| 2,426,535 | 8/1947 | Turkel . |
| 2,623,521 | 12/1952 | Shaw . |
| 2,818,852 | 1/1958 | Kugler . |
| 2,839,049 | 6/1958 | MacLean . |
| 3,477,423 | 11/1969 | Griffith . |
| 3,561,429 | 2/1971 | Jewett et al. . |
| 3,692,020 | 9/1972 | Schied . |
| 3,835,860 | 9/1974 | Garretson . |
| 3,989,033 | 11/1976 | Halpren et al. . |
| 4,230,123 | 10/1980 | Hawkins, Jr. .............. 128/754 |
| 4,266,555 | 5/1981 | Jamshidi .................... 128/753 |
| 4,282,884 | 8/1981 | Boebel ....................... 128/751 |
| 4,345,589 | 8/1982 | Hiltebrandt ................. 128/4 |
| 4,356,828 | 11/1982 | Jamshidi .................... 128/754 |
| 4,396,021 | 8/1983 | Baumgartner ................ 128/754 |
| 4,461,305 | 7/1984 | Cibley ....................... 128/754 |
| 4,517,965 | 5/1985 | Ellison ...................... 128/754 |
| 4,600,014 | 7/1986 | Beraha ....................... 128/754 |
| 4,605,011 | 8/1986 | Naslund ...................... 128/752 |
| 4,619,272 | 10/1986 | Zambelli .................... 128/753 |
| 4,655,226 | 4/1987 | Lee .......................... 128/754 |
| 4,667,684 | 5/1987 | Leigh ........................ 128/754 |
| 4,699,154 | 10/1987 | Lindgren .................... 128/754 |
| 4,723,545 | 2/1988 | Nixon ........................ 128/755 |
| 4,733,671 | 3/1988 | Mehl ......................... 128/754 |
| 4,735,215 | 4/1988 | Goto et al. .................. 128/754 |
| 4,747,414 | 5/1988 | Brossel ...................... 128/754 |
| 4,766,907 | 8/1988 | deGroot et al. .............. 128/754 |
| 4,776,346 | 10/1988 | Beraha et al. ............... 128/754 |
| 4,953,558 | 9/1990 | Akerfelt ..................... 128/754 |
| 4,958,625 | 9/1990 | Bates et al. ................. 128/749 |

FOREIGN PATENT DOCUMENTS

| | | |
|---|---|---|
| 0010321 | 4/1980 | European Pat. Off. . |
| 0031228 | 7/1981 | European Pat. Off. . |
| 1267960 | 6/1961 | France . |
| 88/00297 | 10/1988 | PCT Int'l Appl. . |
| 175611 | 10/1965 | U.S.S.R. . |
| 187228 | 10/1966 | U.S.S.R. . |
| 422414 | 4/1974 | U.S.S.R. . |
| 707576 | 1/1980 | U.S.S.R. . |
| 141108 | 4/1980 | U.S.S.R. . |
| 1009419 | 4/1983 | U.S.S.R. . |

*Primary Examiner*—Max Hindenburg
*Attorney, Agent, or Firm*—Texler, Bushnell, Giangiorgi & Blackstone

[57] ABSTRACT

A tissue sampling instrument or device for use with a two-part needle assembly having an outer cannula and an inner stylet, includes first and second carriage structures for displacing the respective stylet and cannula. The instrument also includes a drive carriage structure which provides separate and sequential engagement and displacement of the two needle carriage structures during operation of the instrument. The drive carriage structure first engages and displaces the stylet carriage, and thereafter engages and displaces the cannula carriage in order to produce sequential motions of the stylet and cannula in the operation to capture the tissue sample. The drive carriage structure also includes means for releasing the engagement of the stylet carriage at the termination of its driven displacement prior to the sequentially successive engagement of the cannula carriage structure. The stylet and cannula carriage structures of the two-part needle assembly can be coupled to enable positively and releasably retaining the two carriage structures together prior to installation of the coupled needle assembly into the instrument housing the drive carriage structure.

13 Claims, 7 Drawing Sheets

INSTRUMENT FOR TISSUE SAMPLING

BACKGROUND OF THE INVENTION

The present invention relates to instruments for obtaining tissue samples to be used for example in biopsy procedures. More particularly, the invention relates to improved instruments for propelling needle assemblies to sample the diagnostic tissue.

In the effort to improve this diagnostic sampling, particularly of prostate tissue, needle assemblies have been developed which capture a longitudinal, or core sample of the tissue which is extracted for diagnosis. Conventionally, the needle assembly has a hollow outer cannula needle through which a cutting, stylet needle is slidably projected to cut and capture a core of the tissue within a notch formed in the inner stylet as described for example in U.S. Pat. No. 4,776,346. The sampling procedure for such a needle assembly requires separate motions of the inner stylet and the outer cannula to accomplish the tissue capture. The instrument described in the aforementioned patent allows a physician to manually perform the dual motions of the needle assembly, however, each motion requires a separate and different manual activation. The separate manual movements to activate the needle operation involve the potential for displacement of the intended needle alignment and motions, and the danger of puncturing organs adjacent to the intended tissue A similar instrument allowing simplified activation of the needle assembly movements is described in U.S. Pat. No. 4,699,154, however, the described instrument requires multiple propulsion springs and release mechanisms in order to produce the needle motions. These disadvantages are eliminated with the instruments in accordance with the present invention.

SUMMARY OF THE INVENTION

In accordance with the present invention, a tissue sampling instrument for use with a two-part needle assembly having an outer cannula and an inner stylet, includes first and second carriage structures for displacing the respective stylet and cannula. The instrument also includes a drive carriage structure which provides separate and sequential engagement and displacement of the two needle carriage structures during operation of the instrument. The drive carriage structure first engages and displaces the stylet carriage, and thereafter engages and displaces the cannula carriage in order to produce sequential motions of the stylet and cannula in the operation to capture the tissue sample. The drive carriage structure also includes means for releasing the engagement of the stylet carriage at the termination of its driven displacement prior to the sequentially successive engagement of the cannula carriage structure.

In a preferred embodiment of the invention, the stylet and cannula carriage structures of the two-part needle assembly are coupled to enable positively and releasably retaining the two carriage structures together prior to installation of the coupled needle assembly into the instrument housing the drive carriage structure. The preferred drive carriage structure includes a deflectable arm structure which engages and drives the first, stylet carriage and then disengages the stylet carriage during the driven displacement of the cannula carriage. The instrument housing provides guide grooves for the displacement of the carriage structures and the deflectable arm structure which will allow variable lengths of stroke for the needle, for example a 25 or 13 mm stroke.

In a particularly preferred embodiment, the drive carriage is propelled by a single drive spring which is expanded and compressed with reversible motions of the drive carriage. A manually slidable cocking member is provided not only to compress the drive spring and slide the drive carriage into position for operating the instrument, but in addition, the cocking member serves as a releasable guard to selectively prevent inadvertent operation of a trigger member which releases the spring compression and drive carriage to initiate the tissue sampling operation. That is to say the device can only be operated when the guard or cocking member has been properly withdrawn from the trigger member.

A particularly preferred embodiment of the tissue sampling instrument also includes a counting/disabling mechanism for repeated tissue sampling operations of the instrument. The counting/disabling mechanism can also be employed to limit the number of successive tissue sampling operations of the instrument, particularly by preventing cocking or full compression of the drive spring after a pre-selected, repetitive sampling operation limit has been reached.

DESCRIPTION OF THE ILLUSTRATED EMBODIMENT

Figure 1:
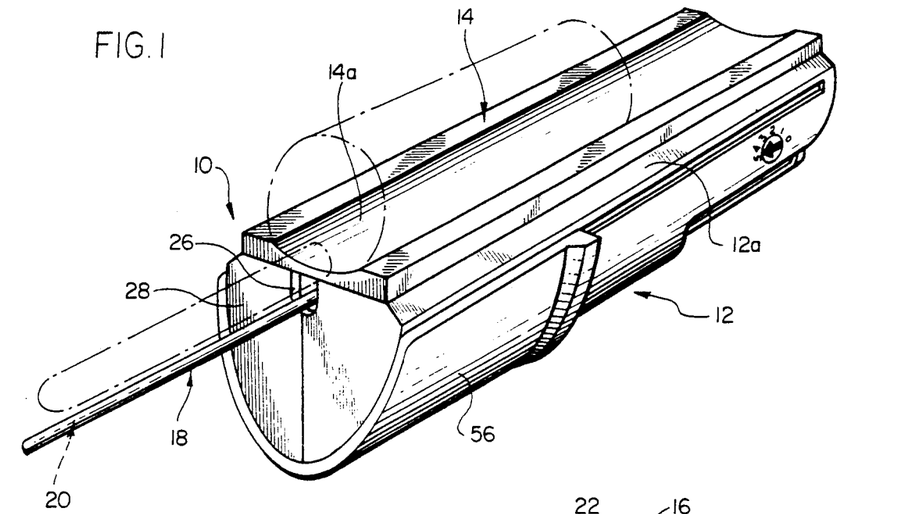
FIG. 1 is a perspective view of one embodiment of the tissue sampling in accordance with the present invention.
Figure 2:
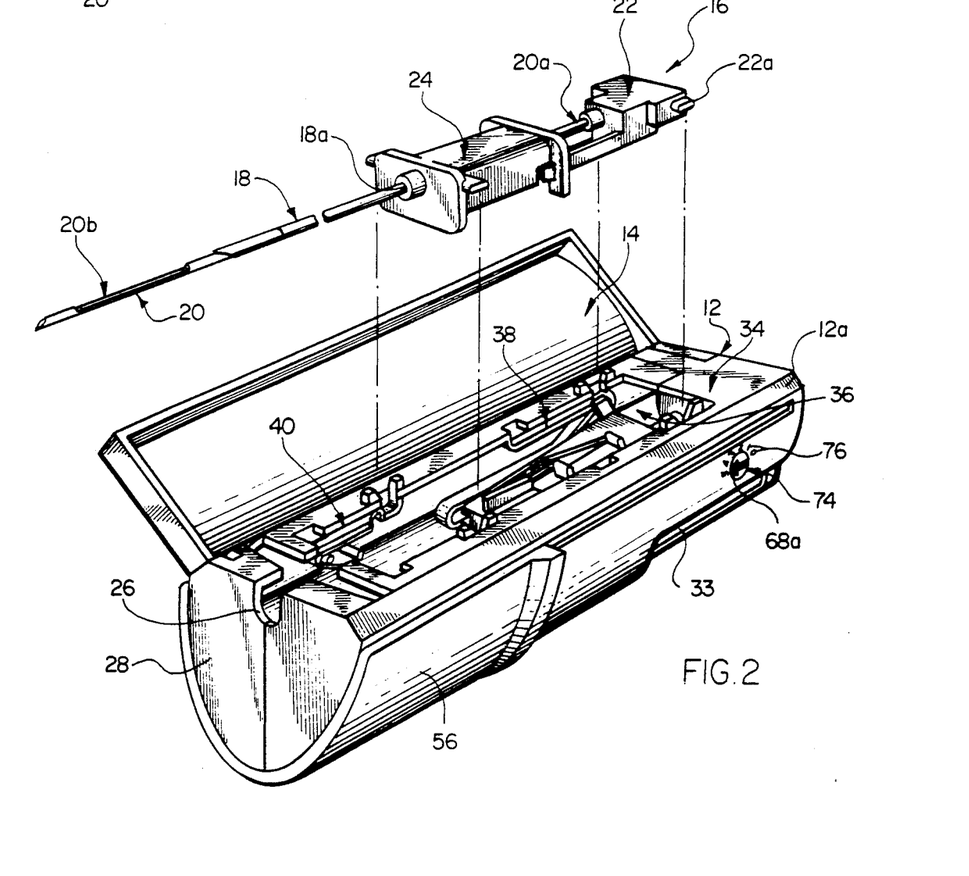
FIG. 2 is a perspective view of the instrument in FIG. 1 and illustrating a needle assembly removed from the housing of the instrument.

Referring to FIGS. 1 and 2, one embodiment of a tissue sampling instrument or actuator in accordance with the present invention is designated generally by reference character 10. The instrument 10 includes a housing 12 which has a hinged cover 14 that opens to enable installation and removal of a needle assembly generally designated by reference character 16. The cover 14 has a shallow channel 14a to accommodate an ultrasound probing instrument, shown in dotted outline, for aiding in location of the tissue to be sampled. The probe portion of the instrument will be disposed closely adjacent the needle assembly 16 due to the groove 14a.

Figure 4:
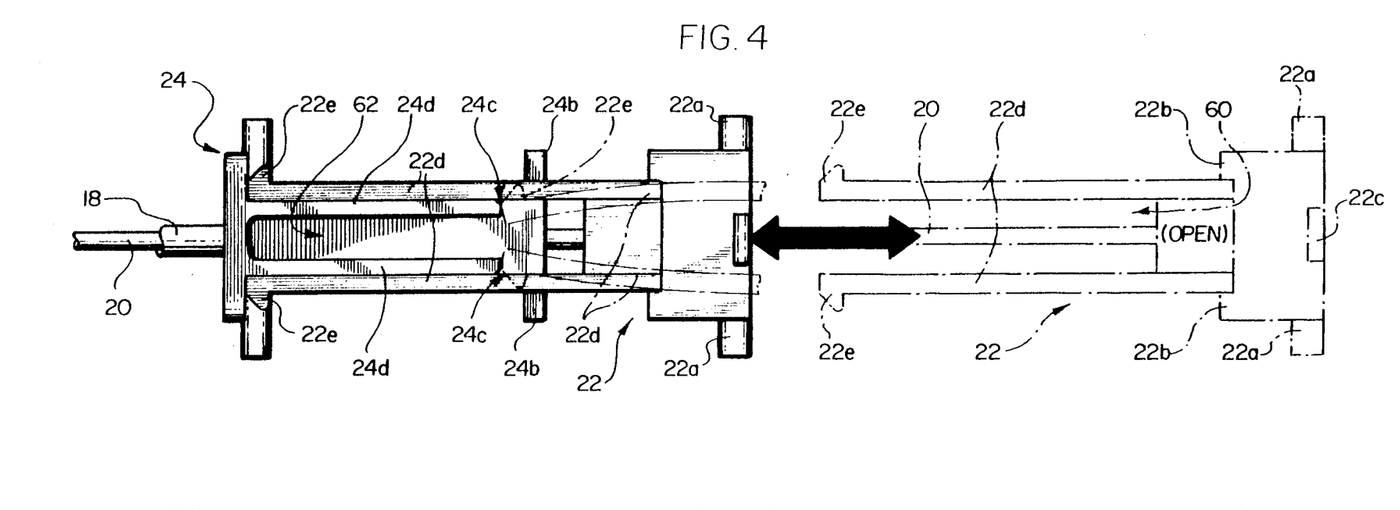
FIG. 4 is a bottom plan view of the carriages in the needle assembly shown in FIGS. 2 and 3.
Figure 8:
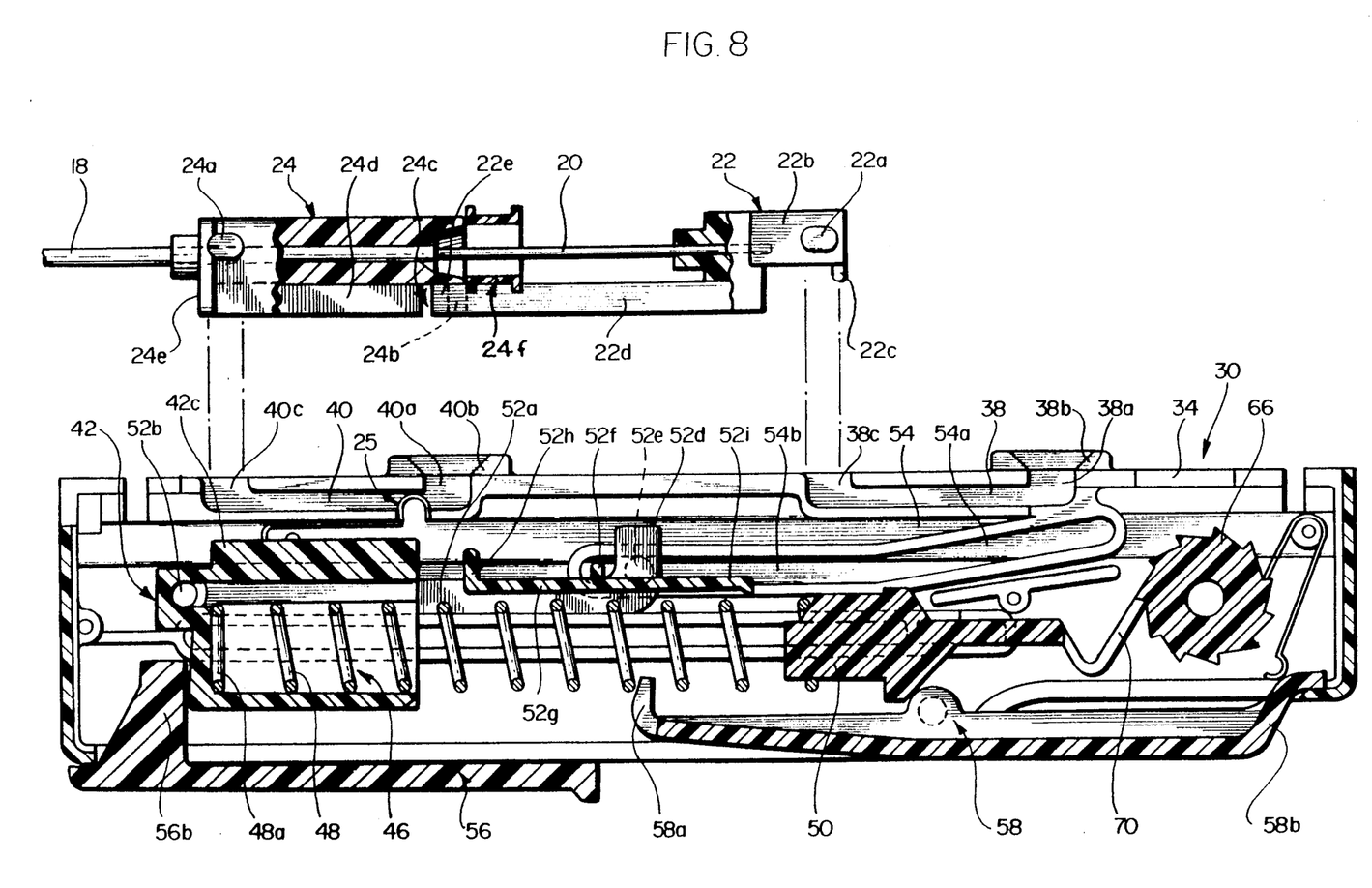
FIG. 8 is a sectional view of the instrument of FIGS. 2 and 3 showing the needle assembly removed from the housing of the instrument.

A bevelled upper edge 12a of the housing 12 at the free edge of the cover 14 facilitates manual access for opening the cover 14. The needle assembly 16 includes an outer cannula 18 through which a stylet 20 is slidably projected to cut and capture a core of the diagnostic tissue, as more fully described hereinafter. The rear end 20a of the stylet 20 is secured within a stylet hub or carriage 22 and the rear end 18a of the cannula 18 is secured within a cannula hub or carriage 24. As best shown in FIGS. 4 and 8, the carriages 22 and 24 are coupled to enable limited relative sliding and displacement of the carriages, and the carriages can be uncoupled to allow the stylet 20 to be entirely withdrawn from the cannula 18 in order to enable the tissue core sample to be removed from the notch 20b in the stylet 20, and also to permit a syringe to be attached to the cannula carriage for obtaining a body fluid sample.

Figure 3:
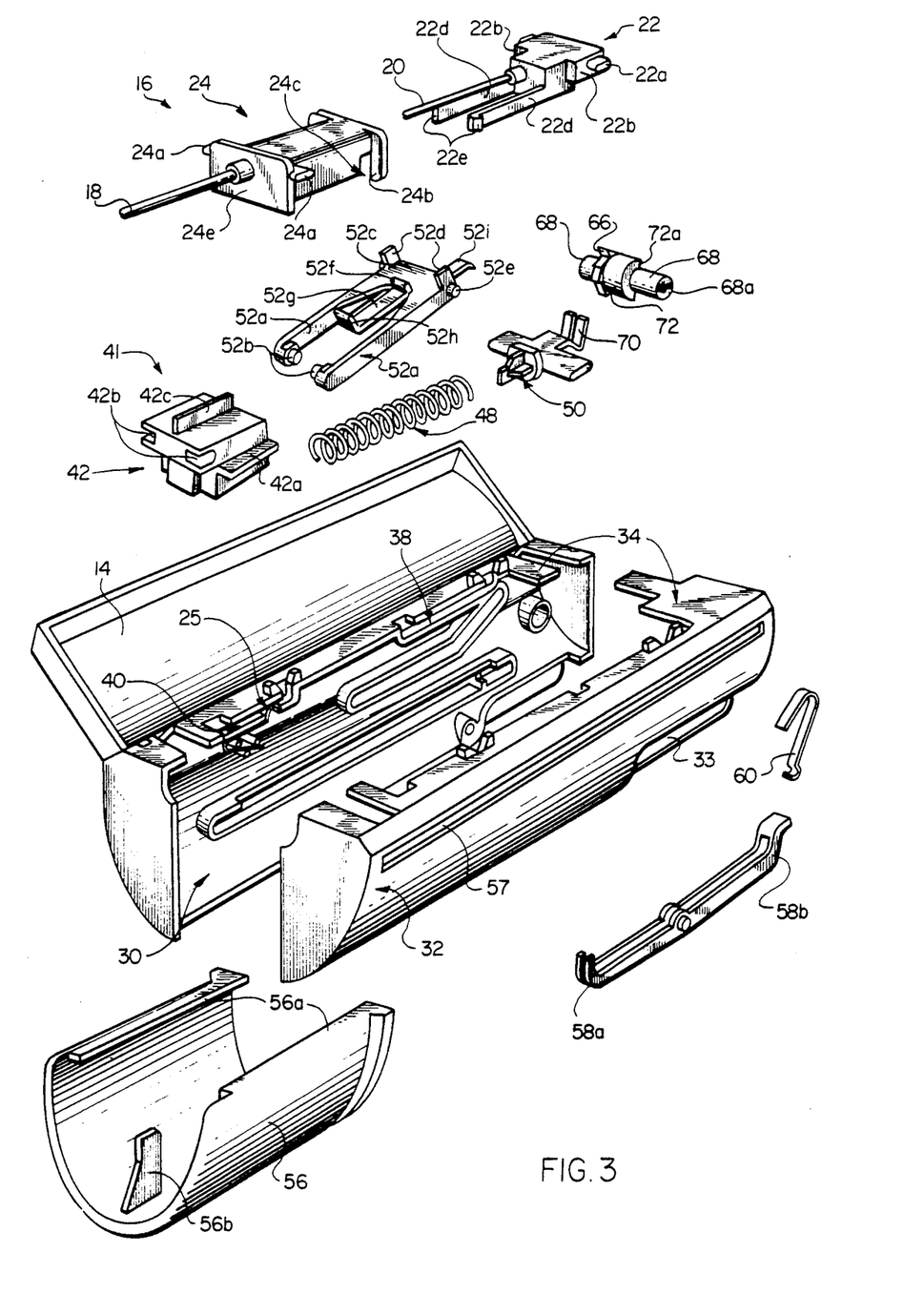
FIG. 3 is an exploded perspective view of the needle assembly and instrument housing of FIGS. 1 and 2.

Referring again to FIG. 2, the needle assembly 16 is vertically lowered or disposed into the opened housing 12 so that the stylet 20 and cannula 18 are laid into and project from a notch 26 formed in the front wall 28 of the housing 12. As best shown in FIG. 3, the housing 12 has opposing side walls 30 and 32 molded as generally vertically split housing halves. The sides 30 and 32 are joined to provide an upper wall 34 which has a large, elongate aperture 36 through which the needle assembly 16 is installed and then removed as shown in FIGS. 2 and 8.

Figure 5:
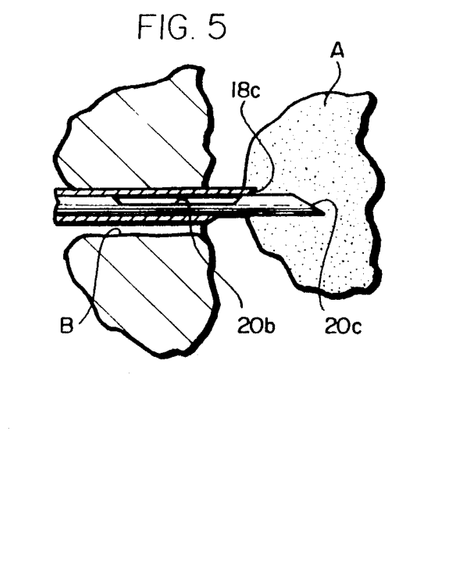
FIGS. 5, 6 and 7 are diagrammatic views illustrating the tissue and tissue sampling operation of the needle assembly and instrument of FIGS. 1-4.
Figure 6:
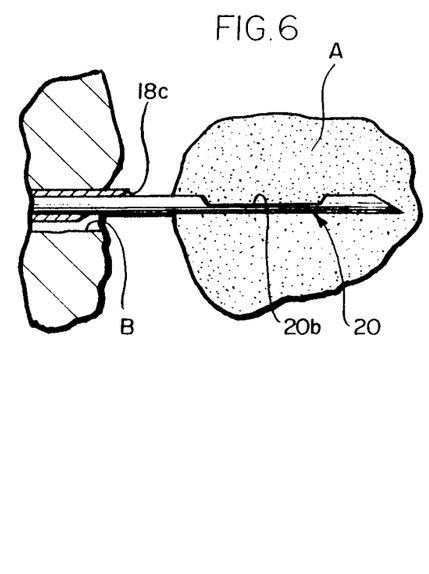
Figure 7:
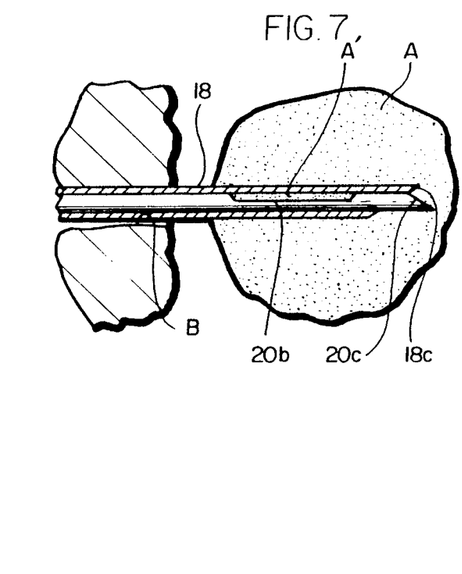

FIGS. 5–7 illustrate representative operating steps and displacements of the stylet 20 and cannula 18, carried on the respective carriages 22 and 24, to obtain a tissue sample core from a prostate gland A. To begin the sampling operation, the stylet notch 20b is covered by the cannula 18 and the sharp, incising stylet end 20c may slightly project from the sharp end 18c of the cannula. With the notch 20b thus covered as shown in FIG. 5, the physician holds the instrument 10 and guides the stylet 20 and cannula 18 into the peritoneal area between the anus and testicles until the stylet end 20c closely approaches (or slightly penetrates) the prostate gland A preferably with the locating aid of, for example, an ultrasound probe, shown in dotted outline in FIG. 1. After locating the gland A the tissue core sampling operation is activated by first driving the displacement of the stylet alone into the prostate gland to a depth at which the prostate tissue prolapses into the stylet notch 20b, as shown in FIG. 6. Thereafter, as shown in FIG. 7, while the stylet 20 remains stationary, the cannula 18 is driven forward telescoping over the stylet 20 so that the sharp cannula end 18c cuts through the tissue and slices the top of the prolapsed tissue portion A' within the specimen notch 20b resulting in the capture of the prolapsed tissue as a longitudinal core sample. The tissue sample A' is retained in the sample notch 20b when the stylet 20 is retracted rearwardly through the cannula 18 and withdrawn therefrom in order to remove the core sample from the notch 20b for the tissue analysis. Preferable, the cannula 18 remains in place upon removal of the stylet in preparation for a further tissue sampling. Obviously, the stylet 20 and cannula 18 can be removed as a unit, if desired. Thus, the separate stylet and cannula motions of the sampling operation require that the stylet carriage 22 move forward and then stop the displacement of the stylet 20 prior to initiation of the forward motion of the cannula carriage 24, as more fully described hereinafter.

As best shown in FIGS. 3 and 8, the carriages 22 and 24 of the needle assembly 16 are guided in their operating displacements by respectively paired guide slots or grooves 38, 38 and 40, 40 which are molded into the housing sides 30 and 32 and located just below opening 36 through the upper wall 34. As best shown in FIG. 8, the guide slots 38 and 40 have respective vertical passageways 38a and 40a and entrance bosses 38b and 40b which align passage of respective bearing pins 22a and 24a formed on the carriages 22 and 24, through the upper wall 34 during the installation of the needle assembly 16. The bearing pins 22a and 24a are supported by and guided within the respective guide grooves 38 and 40 during the operating displacements of the respective carriages 22 and 24 as more fully described hereinafter. FIG. 8 is shown with carriages 22 and 24 removed for viewing clarity.

Referring to FIGS. 3 and 8, within the housing 12 is the drive means or drive assembly for the carriage member 22 and 24, this drive means or drive assembly is designated generally 41. The drive means 41 is comprised primarily of the drive member or structure 42 and the drive trailer or follower 52, which is pivotally attached to the drive member 42. The drive structure 42 has a pair of laterally extending bearing flanges 42a shown in FIG. 3 which are supported and reversibly slide in a pair of opposing, main drive structure guide grooves 44 molded into the housing sides 30 and 32 below the grooves 38 and 40. The drive structure 42 includes a blind cavity 46 which opens to the rear of the structure 42 and in which a helical drive spring 48 is disposed and horizontally projects in the expanded condition of the spring. One end 48a of the spring is secured at the inner end of the cavity 46 and the opposite end of the spring is secured on a stationary anchor member 50, see FIG. 8.

As best shown in FIG. 3, a drive trailer or follower structure generally designated by reference character 52 is pivotably coupled to the drive structure 42. The forward portion of the trailer structure is formed by a pair of spaced trailer arms 52a each having an inwardly extending coupling pin 52b which is pivotally received within sides of the drive carriage 42. The rear end of the trailer structure 52 has a bridge portion 52c which joins the arms 52a and also has a pair of spaced, upstanding drive pins 52d which, as will be detailed hereinafter, engage and drive rear surfaces formed on respective shoulders 22b laterally extending from the upper portion of the stylet carriage 22, during its operating displacement. Below each of the drive pins 52d is a laterally extending cam following pin 52e which is displaced and guided within a respective cam guide groove 54 molded into each of the respective housing sides 30 and 32 between each of the respective drive member guide grooves 44 and the respective grooves 38. As best shown in FIG. 8, the cam guide groove 54 has a forward generally horizontal portion 54b and a rearward, inclined portion 54a, for a purpose to be explained.

Figure 9:
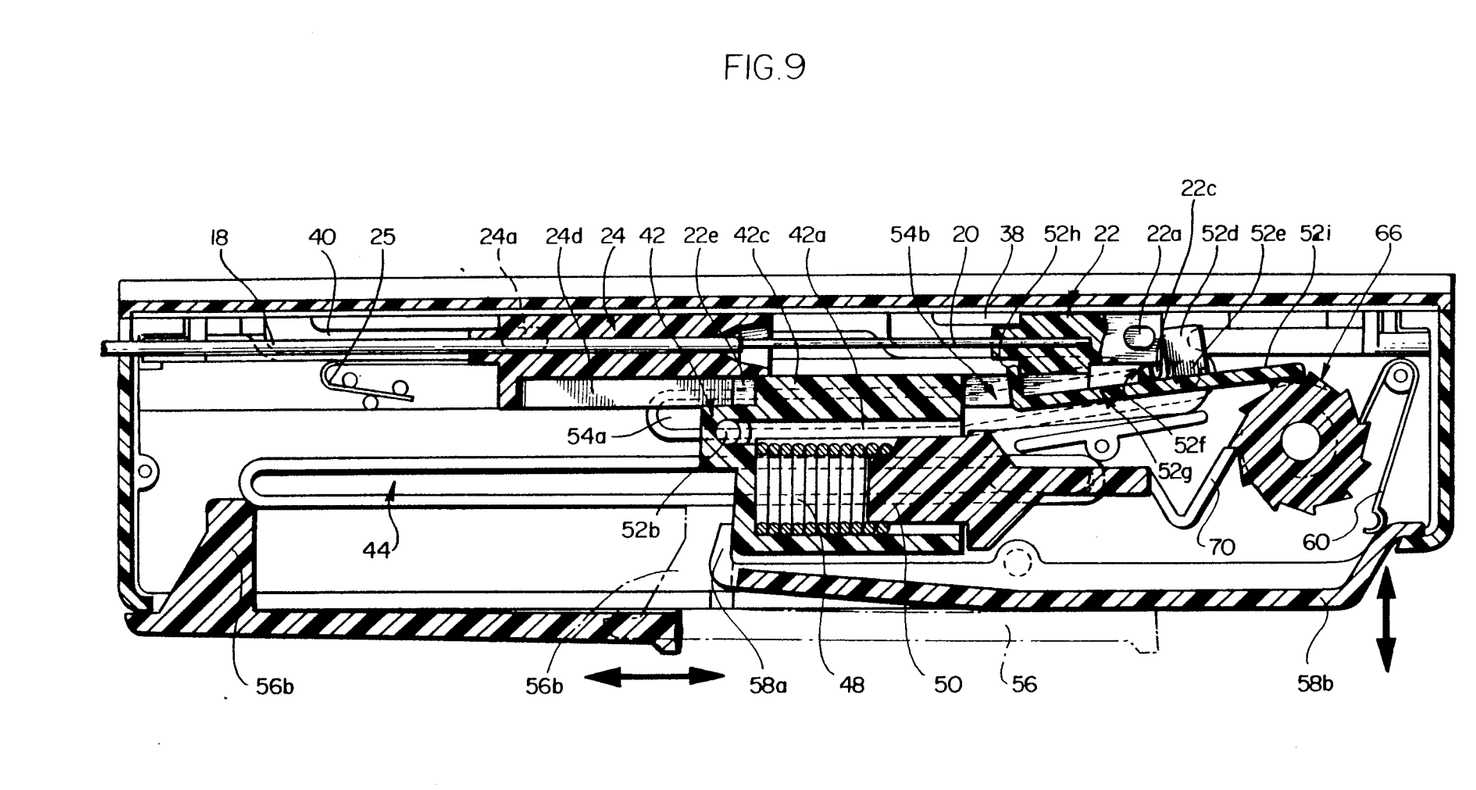
FIG. 9 is a sectional view of the instrument of FIGS. 1-3 and corresponding to the beginning of the tissue sampling operation shown in FIG. 5.

Referring to FIG. 9, the tissue sampling and instrument operation begins with "cocking" the drive member 42 by manually retracting the reversibly slidable cocking member 56 on the outside of the housing 12. The cocking member has inwardly projecting guide flanges 56a which ride in guide grooves 58 formed in the exterior of the respective housing halves 30 and 32 as shown in FIG. 3. The cocking member 56 also has an inwardly projecting drive tongue 56b which engages the front surface of the drive member 42 in order to rearwardly displace the drive member 42 to its power position and thereby compress the helical drive spring 48. The compressed spring 48 is then disposed within cavity 46 when the cocking member 56 is manually retracted from the sectioned, solid line position on the left in FIG. 9 to the "cocked" and guard position shown in phantom line on the right. In the cocking motion, the bevelled lower corner of drive member 42 engages and depresses the forward, bevelled retainer arm portion 58a of the pivotal trigger member 58, against the bias force of the trigger spring 60 imposed on the trigger lever arm portion 58b. When the drive member 42 has reached the fully cocked or power position shown in FIG. 9, the bias force from spring 60 will lift the trigger retainer portion 58a upwardly into engagement with the front of the drive member structure 42 to retain the compression of the helical drive spring 48 and the power position of the drive member 42, under the leveraged force of the spring 60. As shown in FIG. 3, the trigger retainer portion 58a is bifurcated to straddle the drive tongue 56b in the retaining or power position of the drive carriage 42.

Figure 10:
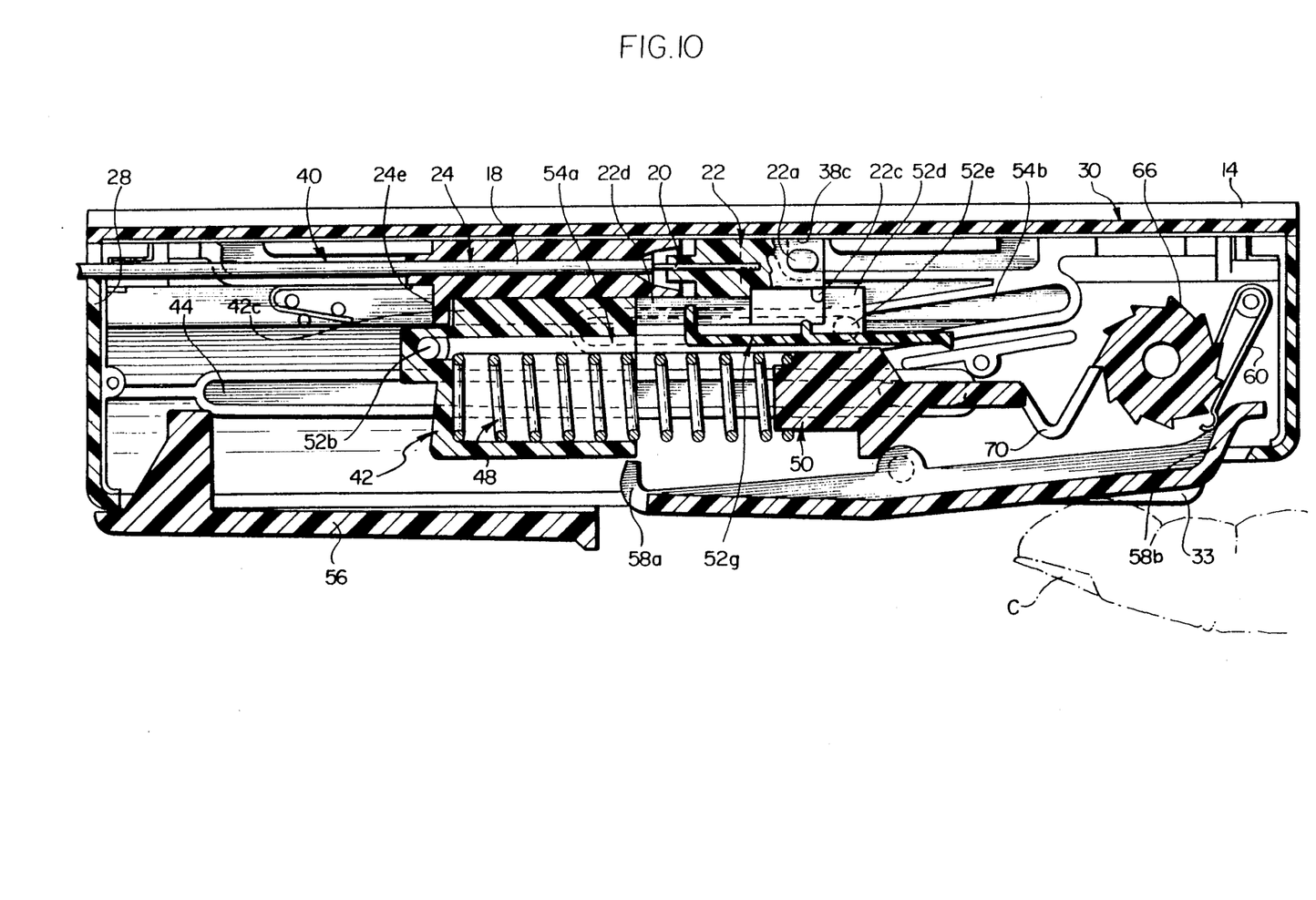
FIG. 10 is a sectional view of the instrument similar to FIG. 9 showing an intermediate stage in the tissue sampling operation of the instrument generally corresponding to FIG. 6.

When the cocking member 56 is retained in the retracted, cocked position below the trigger retainer portion 58a, the cocking member 56 functions as a guard structure to prevent any inadvertent depressing of the trigger retainer portion 58a for release of the drive member 42 and the expansion of the drive spring 48. Thus, when the instrument 10 is ready for operation to begin the tissue sampling procedure for the instrument 10, the cocking member 56 must be moved forward into the leftward, solid line position as shown in FIG. 9 in order to allow the trigger retainer portion 58a to pivot counterclockwise with the physician's manual elevation of the trigger lever arm portion 58b against the bias force of the spring 60 as shown in FIG. 10. Also shown in FIG. 10 as well as in FIGS. 1-3, a trigger guard portion 33 extends from the bottom rear of each of the respective housing sides 30, 32 to flank and conceal the lever arm portion 58b of the trigger except at the free end which is exposed for the deliberate elevation by the physician's finger C.

When the cocking member 56 slides back to compress the drive spring 48 in the "cocking action" as shown in FIG. 9, the trailer guide pins 52e are guided upwardly by the inclined groove portion 54b and lift the drive pins 52d into position for engagement with the rear surface of the carriage shoulders 22b on the stylet carriage 22 which is thereafter installed with the coupled cannula carriage 24 into the previously cocked, power position of the drive carriage 42 and trailer member 52. The installation of the carriages 22 pins 22a and 24a through the respective pairs of guide slots 38a and 40a at the rear of the respective guide grooves 38 and 40 as indicated in FIG. 2. When shorter lengths of the stylet 20 and cannula 18 and of the operating displacements of the needle assembly 16 are needed, adjustments can be made in the location of the guide slots 38a and 40a to reduce the displacement lengths of the carriages 22 and 24 without requiring dimensional modifications of the drive member 42 and trailer member 52.

As shown in FIGS. 3 and 8, a retainer spring 25 engages and restrains the bearing pin 24a to hold the cannula carriage 24 in its initial, installed position until the spring 25 yields downwardly to allow the pin 24a to pass over when the carriage 24 is driven during its operating displacement. Additionally, the stylet carriage 22 is provided with a retainer flange 22c which extends downwardly and centrally from the rear surface of the carriage and engages behind a retainer foot 52f extending upwardly from a retainer tongue 52g centrally extending between the trailer arms 52a. The trailer retaining foot 52f serves to prevent any forward displacement of the stylet carriage 22 within the housing 12 in the event that the entire housing 12 and needle assembly 16 are slightly withdrawn from the patient's tissue for adjusting the needle location prior to the operating displacements of the carriages in the tissue sampling operation. Similarly, one or more additional retainer feet 52h can be provided on the tongue 52g and trailer at the appropriate locations to accommodate variation in the initial position of the stylet carriage 22 for shortened needle assemblies and operating displacements.

Referring again to FIGS. 5-7, after installing the needle assembly into the housing 12 in which the drive carriage 42 has been cocked into the power position as shown in FIG. 9, the sample notch 20b is covered by the cannula 18 and the entire housing 12 can be manipulated to guide the stylet and cannula ends to the initial penetration of the prostate gland with the cocking member 56 in the retracted, trigger guarding position shown in FIG. 9. The physician can then slide the cocking member forward to free the pivotal motion of the trigger member 58 and then manually press the trigger lever arm portion 58b upwardly, for example with the forefinger. The disengagement of the trigger retainer portion 58a will release the compression of the drive spring 48 which will accordingly displace the drive member 42 leftwardly as shown in FIG. 10 and the coupled trailer drive pins 52d will then drive the stylet carriage 22 to the position shown in FIG. 10 corresponding to penetration of the tissue by stylet notch 20b as shown in FIG. 6. At this point, the end of the stylet carriage guide groove 38 restrains further forward motion of the bearing pin 22a so that the stylet carriage 22 and stylet 20 arrive at their terminal forward positions as shown in FIGS. 10 and 6 respectively. During this forward operating displacement of the stylet 20 and stylet carriage 22, the cannula 18 and cannula carriage 24 have remained stationary as reflected in the comparison of FIGS. 9 and 10 as well as FIGS. 5 and 6. Moreover, during the stylet carriage displacement, the trailer guide pins 52e have been gradually guided downwardly by forward motion through the inclined portion 54a of the cam groove 54 which causes the same gradual descent of the trailer drive pin 52d to the point shown in FIG. 10 where the drive pins 52d entirely disengage from the stylet carriage shoulders 22b and the forward displacement of the stylet carriage 22 has been terminated at the end 38c of the guide groove 38. At this point, the trailer drive pins 52d are no longer engaged with the stylet carriage 22 and slide beneath the carriage shoulders 22b during the further forward motion of the trailer 52 with the remainder of the forward motion of the drive member 42 and further expansion of the drive spring 48, continuing as described hereinafter.

Figure 11:
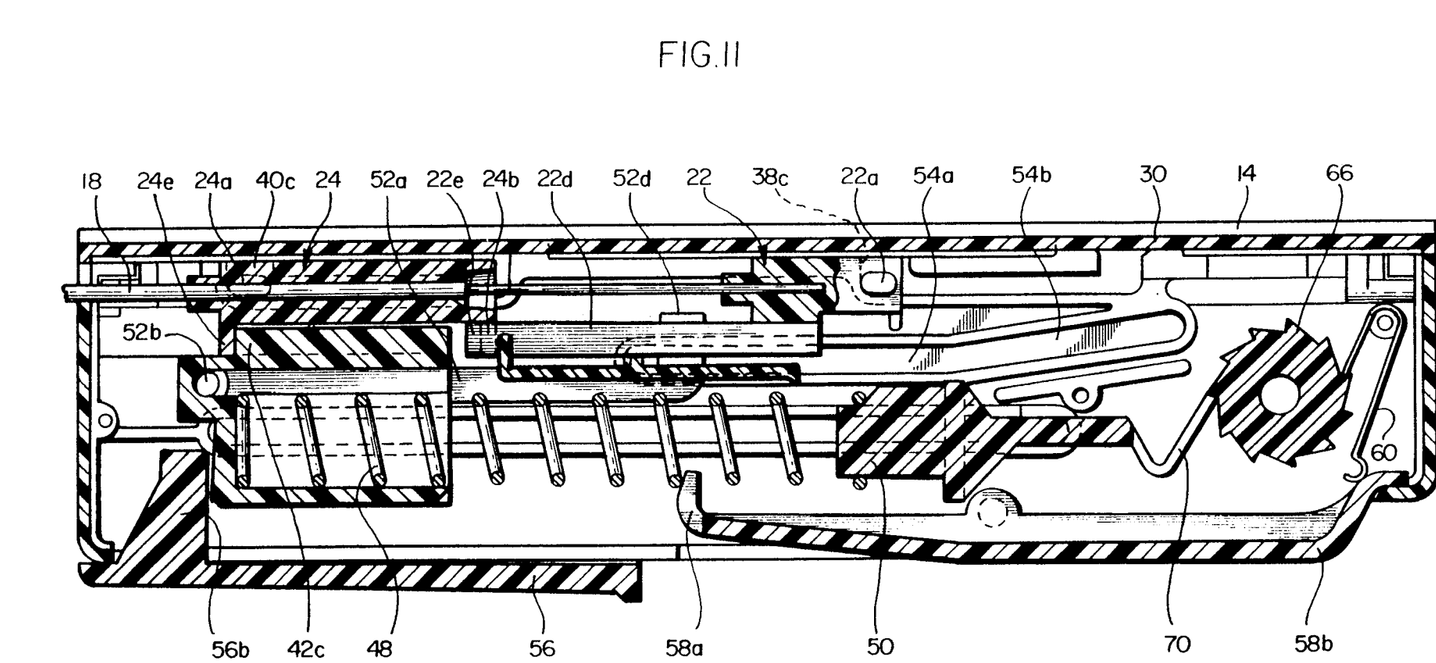
FIG. 11 is a sectional view of the instrument similar to FIGS. 9 and 10 and showing the instrument at the completion of the tissue sampling operation generally corresponding to FIG. 7.

As shown in FIG. 4, the bottom of the stylet carriage 22 is slotted at 60 to provide clearance for passage of the trailer retainer tongue 52g and feet 52f and 52h therethrough between spaced guide arms 22d extending from the stylet carriage 22, during the forward motion of the trailer member 52. As shown in FIGS. 10 and 11, as the trailer retainer feet 52f and 52h pass between the guide arms 22d, the trailer drive pins 52d straddle both of the guide arms 22d during such passage.

Referring again to FIG. 4, the stylet slide 22 is molded from suitable resin, such as ABS, which will enable the guide arms 22d to be resiliently deflectable and enable the coupling ends 22e to be manually pinched toward one another. In the pinched condition, as shown in the phantom position on the left in FIG. 4, both of the coupling ends 22e an be passed through the separation space between locking posts 24b formed at the rear end of the cannula carriage 24, after which release of the pinching force will allow each of the coupling ends 22e to pass outwardly through a respective gap 24c (best shown in FIG. 3) in each of the lower side walls 24d. The stylet carriage guide arms 22d are spaced for sliding engagement against the respective lower side walls 24d of the cannula carriage 24, and the coupling of the carriages 22 and 24 is maintained by abutment of coupling ends 22e against the locking post 24b. However, the carriages 22 and 24 can be uncoupled, by manually pinching the guide arms 22d and guiding the coupling ends 22e inwardly through the same respective gaps 24c and withdrawing then through separation spaced between the locking posts 24b in reversal of the coupling procedure. The uncoupling of the carriages 22 and 24 will be particularly beneficial when, after completing the tissue sampling displacements of the stylet 20 and cannula 18 as shown in FIG. 7, the stylet and tissue sample A' are withdrawn rearwardly and removed from the cannula 18 which is maintained in the tissue penetration position; this allows the same or a new stylet 20 to be inserted through the same cannula 18, and the new stylet carriage 22 can be coupled to the cannula carriage 24 and then reinstalled into the housing 12 in which the drive member 42 and spring 48 have been previously re-cocked. The second, successive carriage displacement operation enables obtaining a second, perhaps deeper tissue core sample without the necessity to redetermine the proper location which has been maintained by the original cannula.

Referring again to FIG. 10, the drive member 42 has a centrally upstanding drive flange 42c which is located between the guide arms 22d of the stylet carriage in the "cocked" or power position shown in FIG. 9, and therefore during movement of drive member 42 and trailer 52 only the trailer drive pins 52d engage and drive the stylet carriage 22. During the displacement of the stylet carriage 22 between the positions shown in FIGS. 9 and 10, the drive flange 42c travels forwardly through a clearance slot 62 between the lower walls 24d of the cannula carriage 24 best shown in FIG. 4; however, as shown in FIG. 10, at the point where the termination of the stylet carriage displacement is reached, the drive flange 42c on the drive carriage 42 will approach and then impact the lower front wall 24e of the cannula carriage 24 which forms the ends of the cannula carriage lower walls 24d, 24d. Thereafter, upon continued movement of drive member 42, the drive flange 42c will then drive the cannula carriage 24 from the position shown in FIG. 10 to the position shown in FIG. 11 corresponding to the slicing motion of the displaced cannula end 18c between the positions shown in FIGS. 6 and 7 to complete the capture of the tissue core sample A' within the sampling notch 20b. As additionally reflected in FIGS. 10 and 11, during the displacement of the cannula carriage 24, the stylet carriage 22 remains stationary in its terminal position as further reflected in FIGS. 6 and 7.

Once the operating displacements of the carriages 22 and 24 have been completed as shown in FIG. 11, both carriages 22 and 24, and the needle assembly 16 generally, can be removed from the housing 12 while both the stylet 20 and cannula 18 remain with the patient tissue, by merely lowering the housing 12 so that the respective carriage bearing pins 22a and 24a are released through the respective forward removal slots 38c and 40c of the guide grooves 38 and 40 as shown in FIG. 8. Alternatively, both the stylet and cannula can be removed from the patient tissue while the needle assembly 16 remains installed in the housing 12, merely by retracting the entire housing 12.

The needle assembly 16 as shown in FIGS. 1, 3 and 8, is of novel design. As noted above, the needle assembly 16 includes the inner stylet 20, the outer cannula 18, and the respective carriage portions 22 and 24. The carriage portions 22 and 24 are releasably interconnected for relative movement by a pair of guide arms 22d, each of which has a hook portion or end 22e on the distal end thereof, and are integrally formed with the stylet carriage 22. The respective guide arms 22d are received in slots or gaps 24c formed in the end face of the carriage 24. The hook-shaped ends 22e serve to interconnect the respective carriage member 22 and 24, while permitting relative movement. Further, as the carriage 22 moves toward carriage 24, the guide arms 22d which are flexible, will slide in the slots or gaps 24c until the ends 22e abut the flange portion 24e on the inner end of carriage 24, such that flange 24e serves as a stop to limit the movement of the stylet carriage 22 toward the cannula carriage 24.

As noted above, the guide arms 22d are flexible. As such they can be operated to disengage said guide arms from the cannula carriage 24. Thus, after the device 10 has been operated as described above to sever a portion of prolapsed tissue for disposition in the specimen notch 20b, FIG. 7, the biopsy needle assembly 16 may be disengaged from the instrument 10. The surgeon then can disconnect the respective carriages 22 or 24 by depressing guide arms 22d and withdrawing the stylet 20 form the cannula 18, while leaving the cannula 20 in place. The tissue sample is then removed from the specimen notch 20b.

At this point the surgeon has several options. He may reinsert the stylet 20 into the cannula 18, engage the needle assembly 16 with the instrument 10 and take a second or additional tissue samples, as needed. Also, rather than re-assemble the stylet and cannula, the surgeon may desire to take a body fluid sample from the area wherein the tissue sample has been removed. In this regard, the cannula carriage 24 may be provided with a standard Luer fitting 24f, FIG. 8, permitting the attachment of a syringe (not shown) to the cannula carriage or hub 24, for removal of a fluid sample. Further, it should be noted that the needle assembly 16 may also be operated manually by the surgeon that is, without assembly to the device 10.

Referring again to FIGS. 3 and 8, an additional counting and lock-up structure 64 can be incorporated in the instrument 10 in one embodiment in which a toothed, ratchet wheel 66 on an integral bearing shaft 68 is journalled in the housing halves 30 and 32. Each time the drive member 42 is cocked from the position shown in FIG. 8 to the position shown in FIG. 9, a ratchet arm 52i projecting rearwardly from the trailer 52 will engage a tooth of the ratchet wheel 66 which is then indexed in a clockwise rotation as viewed in FIG. 8 with each rearward cocking motion of the trailer and ratchet arm 52i. A ratchet spring 70 maintains the ratchet bias for the clockwise rotation of the ratchet wheel 66. In the illustrated embodiment, the ratchet spring 70 is shown as a resilient arm formed on the stationary anchor member 50, although suitable alternative ratchet springs such as a coil spring can be substituted for the arm 70. A lock-up boss 72 is integrally mounted on the bearing shaft 68 adjacent the ratchet wheel 66 as shown in FIG. 3. The lock-up boss 72 has a radially extending flat surface 72a which is arranged on the bearing shaft 68 at an angular location such that a selective preset number of index rotations of the ratchet wheel 66 will bring the flat surface 72a into abutment against a stop member (not shown) extending from the housing half 32 which will then prevent further rotation of the ratchet wheel 66. Accordingly, the resulting obstruction of the full rearward motion of the ratchet arm 52i will prevent completion of the cocking motion of the trailer 5 and drive member 42 so that the instrument 10 cannot be operated in excess of the preset limit on the number of repetitive cocking movements.

As best shown in FIG. 2, the housing halves 30 and 32 are provided with respective apertures 74 which reveal the indicator arrows 68a on the ends of the bearing shaft 68. Rotation of the bearing shaft 68 with each index of the ratchet wheel 66 will also index the direction of the arrow to indicate to the physician the remaining number of successive cocking operations by numeral sequence 76 provided on each of the housing halves 30, 32 surrounding the respective apertures 74.

While particular embodiments of the tissue sampling instrument have been described herein, it will be obvious to those skilled in the art that changes and modifications in various aspects may be made without departing from the broad scope of the invention.

Consequently, the scope of the invention is not limited by any particular embodiment but is defined by the appended claims and the equivalents thereof.

The invention is claimed as follows:

1. A tissue sampling instrument for use with a two-part needle assembly having an outer, first needle cannula within which an inner second needle stylet is axially translated, said instrument comprising:
    a) a first carriage structure affixed to and for carrying and displacing said inner stylet through said outer cannula;
    b) second carriage structure affixed to and for carrying and displacing said outer cannula relative to said inner stylet; and
    c) drive means comprising a drive member structure separately and sequentially engageable with and disengageable from both of said first and second carriage structures to enable engaging and displacing said first carriage structure followed by engaging and displacing said second carriage structure in order to produce sequential motions of the stylet and cannula and capture of a tissue sample therebetween.

2. The instrument according to claim 1, wherein said drive means comprises engagement and release means for terminating said driven displacement of said first carriage structure prior to said sequentially successive driven displacement of said second carriage structure.

3. The instrument according to claim 2, wherein said release means comprises a deflectable arm member disengageable from drive engagement with said first carriage structure for driving said respective displacement thereof.

4. The instrument according to claim 3, wherein said arm member comprises guide means for deflection and said disengagement of said arm member.

5. The instrument according to claim 4, wherein said guide means comprises at least one cam follower.

6. An instrument according to claim 5 wherein said cam follower is displaceable through a guiding cam groove formed in said instrument.

7. An instrument according to claim 1, wherein said drive means comprises spring means for propelling the displacements of said first and second carriage structures, and wherein said instrument further comprises trigger means for releasing said propulsion by said spring means; a cocking member movable to energize said spring means, said cocking member being selectively and reversibly movable between a guard position in which said spring means is fully energized and in which said cocking member blocks release of said propulsion by said trigger means, and a retracted position in which said cocking member unblocks release of said propulsion by said trigger means.

8. An instrument according to claim 1 further comprising coupling means for positively and releasably retaining said first and second carriage structures in coupled assembly apart from said drive means to enable said coupled assembly prior to installation thereof into said tissue sampling instrument.

9. An instrument according to claim 8, further comprising a guide member projecting from one of said carriage structures, said guide member being slidably received by guide structure formed on the other of said carriage structures for guiding said relative displacements of said coupled carriage structures during tissue sampling operation thereof.

10. A carriage assembly according to claim 8, wherein said coupling means comprises a resiliently deflectable coupling member for selectively coupling and uncoupling of said carriage structures.

11. A tissue sampling instrument for use with a two-part needle assembly having an outer, first needle cannula within which an inner second needle stylet is axially translated, said instrument comprising:
    a) a first carriage structure affixed to and for carrying and displacing said inner stylet through said outer cannula;
    b) second carriage structure affixed to and for carrying and displacing said outer cannula relative to said inner stylet; and
    c) drive means for separately and sequentially engaging and displacing said first carriage structure followed by engaging and displacing said second carriage structure in order to produce sequential motions of the stylet and cannula and capture of a tissue sample therebetween, wherein said drive means comprises a single spring member for propelling said displacements of both said first and second carriage structures.

12. A tissue sampling instrument for use with a two-part needle assembly having an outer, first needle cannula within which an inner second needle stylet is axially translated, said instrument comprising:
    a) a first carriage structure affixed to and for carrying and displacing said inner stylet through said outer cannula;
    b) second carriage structure affixed to and for carrying and displacing said outer cannula relative to said inner stylet; and
    c) drive means for separately and sequentially engaging and displacing said first carriage structure followed by engaging and displacing said second carriage structure in order to produce sequential motions of the stylet and cannula and capture of a tissue sample therebetween, wherein said drive means comprises: a single spring member; a drive assembly movable between a first and second position propelled by said spring member, and including a trailer member adapted when said drive assembly is in said first position to engage said first, stylet carriage structure such that the motion of said drive assembly from said first position toward said second position advances said first stylet carriage structure; cam means for disengaging said trailer member from said first stylet carriage structure at an intermediate point in said movement of said drive assembly thereby terminating the advance movement of said first stylet carriage structure; and means on said drive assembly for engaging said second cannula carriage structure at an intermediate point in said movement of said drive assembly toward said second position, and for propelling said advancing movement of said second cannula carriage structure after said termination of the advancing movement of said first, stylet carriage structure to cause said tissue sample capture between said stylet and cannula.

13. A tissue sampling instrument for use with a two-part needle assembly having an outer, first needle cannula within which an inner second needle stylet is axially translated, said instrument comprising:
a) a first carriage structure affixed to and for carrying and displacing said inner stylet through said outer cannula;
b) second carriage structure affixed to and for carrying and displacing said outer cannula relative to said inner stylet; and
c) drive means for separately and sequentially engaging and displacing said first carriage structure followed by engaging and displacing said second carriage structure in order to produce sequential motions of the stylet and cannula and capture of a tissue sample therebetween, further comprising counting and disabling means for registering the number of successive tissue sampling operations of said instrument and for disabling said instrument after a selected number of said operations have been completed.

* * * * *

UNITED STATES PATENT AND TRADEMARK OFFICE
CERTIFICATE OF CORRECTION

PATENT NO. : 5,121,751

DATED : June 16, 1992

INVENTOR(S) : Joseph V. Ranalletta

It is certified that error appears in the above-identified patent and that said Letters Patent is hereby corrected as shown below:

On title page, item [19] and item [75],

Inventor's name "Joseph V. Panalletta" should be
-- Joseph V. Ranalletta --

Column 4, Line 41 "within sides of the drive carriage 42." should be -- within a respective coupling mortise 42a formed in the opposite sides of the drive carriage 42. --

Column 5, Line 50 "The installation of the carriages 22 pins 22a and 24a" should be -- The installation of the carriages 22 and 24 is guided by lowering the respective pairs of bearing pins 22a and 24a --

UNITED STATES PATENT AND TRADEMARK OFFICE
CERTIFICATE OF CORRECTION

PATENT NO. : 5,121,751
DATED : June 16, 1992
INVENTOR(S) : Joseph V. Ranalletta

It is certified that error appears in the above-indentified patent and that said Letters Patent is hereby corrected as shown below:

Column 9, Line 14 "completion of the cocking motion of the trailer 5 and " should be -- completion of the cocking motion of the trailer 52 and --

Signed and Sealed this

Third Day of August, 1993

Attest:

MICHAEL K. KIRK

Attesting Officer

Acting Commissioner of Patents and Trademarks